United States Patent [19]

Gatenbeck et al.

[11] 3,963,572

[45] June 15, 1976

[54] FERMENTATIVE PROCESS FOR THE PRODUCTION OF L-TRYPTOPHAN AND ITS DERIVATIVES

[75] Inventors: Sten Vilhelm Gatenbeck, Taby; Per Olof Hedman, Johanneshov, both of Sweden

[73] Assignee: AB Bofors, Bofors, Sweden

[22] Filed: Feb. 28, 1975

[21] Appl. No.: 554,344

[30] Foreign Application Priority Data

Mar. 5, 1974 Sweden.............................. 7402889

[52] U.S. Cl................................. 195/28 N; 195/29
[51] Int. Cl.².......................................... C12D 13/06
[58] Field of Search........... 195/28 R, 29, 30, 28 N, 195/47

[56] References Cited

UNITED STATES PATENTS

| | | | |
|---|---|---|---|
| 2,999,051 | 9/1961 | Malin.................................... | 195/29 |
| 3,808,101 | 4/1974 | Enei et al.............................. | 195/29 |

*Primary Examiner*—A. Louis Monacell
*Assistant Examiner*—Robert J. Warden
*Attorney, Agent, or Firm*—Pollock, Vande Sande & Priddy

[57] ABSTRACT

Fermentation process for preparation of L-tryptophan and its derivatives from indole or derivatives thereof wherein the fermentation is carried out in a substrate with methanol as the main source for carbon and is carried out using a certain type of methanol using bacteria.

21 Claims, No Drawings

FERMENTATIVE PROCESS FOR THE PRODUCTION OF L-TRYPTOPHAN AND ITS DERIVATIVES

This invention involves the process for the fermentative production of L-tryptophan and derivatives thereof. A large number of fermentative procedures involving different yeast and bacteria isolates are already known for the production of L-tryptophan. Indole is used in most cases as precursor. The processess further involve the use of normal fermentative substrates, including for example yeast extract, meat extract, corn steep liquor, carbohydrate or some other complex nutritional preparation which as a rule constitutes difficulties in reproducibility together with limitations concerning the capacity for production.

The present invention has now made it possible for the fermentative production of L-tryptophan and derivatives thereof with good reproducibility and production capacity by the use of methanol as the source of carbon for the microorganisms. Methanol is a very cheap carbon source for the production of microbial cell mass, and in addition has a stable price which is relatively low since the substance can be manufactured by the oxidation of methane or by the catalytic reaction between hydrogen and carbonmonoxide.

It has however become evident according to the present work that not all methanol utilizing microorganisms can be employed, but- instead one must differentiate between two different reaction pathways for the assimilation of methanol.

The first of these pathways which is especially apparent, involves certain microorganisms which are capable of using methanol by oxidizing it to formaldehyde and partly to carbondioxide. The formaldehyde is then fixed by the metabolic activities of microorganisms by the known serine hydroxymethyltransferase reaction according to the following sequence.

tetrahydrofolicacid: CHO + glycine Serine + tetrahydrofolicacid

The glycine which is consumed in this reaction is then again synthesized from methanol, and this happens in accordance with isotopic experimentation by the below given reaction sequence.

cheap raw material and partly due to the natural maximum production of L-serine.

The other pathway for the assimilation of methanol by microorganisms, which among other things has been observed with certain yeast species and some bacteria implies that microorganisms during the utilization of methanol as a carbon source generally metabolize it by the sugar phosphate pathway. This pathway implies that the formaldehyde which is built by the initial oxidation of methanol condenses with ribose-5-phosphate during the synthesis of allulose-6-phosphate. The latter substance isomerises subsequently with fructose-6-phosphate, whereupon the metabolism takes place normally. Ribose-5-phosphate is built up again through the oxidative decomposition of glucose and according to the pentose cycle by the following sequence

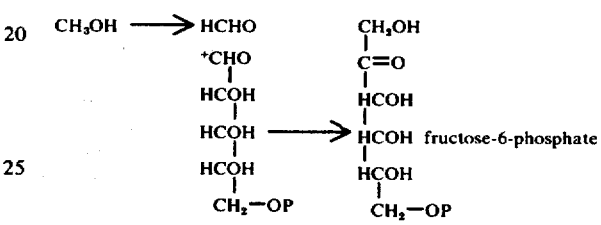

These methanol utilizing microorganisms which metabolize according to the last mentioned pathway are very bad tryptophan producers, when indole is used as a precursor. It is thus, completely, necessary in accordance with what is prescribed by the present invention to use such microorganisms (in the fermentative production of L-tryptophan and derivatives thereof) capable of utilizing methanol as a carbon source which can react via the serine pathway.

A preferable procedure for the fermentative production of tryptophan and its derivatives according to the present invention implies that one under aerobic conditions, submerged in the fermentor grow such isolates of the families Pseudomonas and Methylomonas that are able to utilize methanol as the carbon source via serine. This process can be accomplished either by batch culture or by continuous culture. A mineral salt solution is used as the substrate with a composition as described in

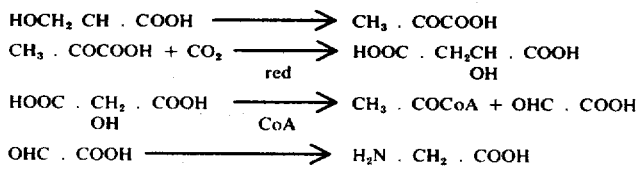

The building up of serine is an absolute prerequisite in order for the microorganism to be able to utilize methanol as the sole carbon source. The intensity of this endogenous serine production becomes thus very high, and this has earlier been a limiting factor in the microbial production of L-tryptophan by the addition of indole as a precursor.

One has in this manner by the introduction of a methanol utilizing bacteria for the fermentative production of L-tryptophan, according to the present invention, obtained a process which is based partly upon a very the enclosed example. No organic substrate component need to be included with the exception of methanol and indole. The growth is suitably accomplished within a temperature interval of between 18°–45°C, therewith preferably a temperature of between 25°–30°C should be employed. The pH must be carefully regulated continuously during the cultivation, and ought to be held within an interval of 5.5–8.5 and preferably between 6.5–7.5.

The supply of methanol should be carried out continuously and this regardless whether it is batch or continuous culture. The methanol concentration should not exceed the marginal toxic value for the cultured isolate, but should lie about the optimal value for tryptophan production. The marginal toxic value for these microorganisms, which are used in this connection, lies around 5 vol-% methanol. The suitable concentration of methanol for optimal production of tryptophan lies between 0.1 and 1.0 % and preferably around 0.5 vol-% methanol.

Because of the fact that the optimal production of tryptophan is dependent upon the relatively low methanol concentrations, where the optimal value lies, it is especially important that the concentration of methanol is kept constantly within the above mentioned values. It is thus necessary for a continuouous automatic analysis of methanol. Several methods for such an analysis are described in the literature related to this subject, and the method which has been used here is based on gaschromatography.

In this study indole or an indole derivative is used as a tryptophanprecursor, these being supplied continuously.

Since the indole concentration is very critical for the process its concentration must also be regulated with the aid of continuous automatic analysis. The concentration of free indole in the culture medium must be kept below a value of 500 mg/l.

The production can be accomplished by an aerobic process, air being supplied by a conventional method and then distributed by a turbine agitator.

The culturing should be carried out under oxygen limiting conditions, owing to the sensitivity of tryptophan for oxidative decomposition.

The period of growth ought to lie between 30 and 90 hours with batch culture.

After the cells have been separated an ionexchanger is used for the isolation and purification of produced tryptophan. Through the usage of methanol as the carbon source in the substrate, and a microorganism which metabolize methanol by the serine pathway, a process has been brought forth by the present work which partly utilizes a much cheaper substrate and partly steers the organism metabolism towards an intensive L-serine production with an effective transformation of indole respectively indole derivatives to tryptophan respectively tryptophan derivative as result.

The production of serine and therewith the production capacity of tryptophan can further be increased by the addition of glycine.

The invention shall now be more closely described under the direction to the following examples, where the examples 1 to 6 and 8 refer to microorganisms which work according to the serine pathway, wheras on the other hand, the example 7 refers to a microorganism which does not assimilate methanol via serine, but instead goes via the allulose pathway.

EXAMPLE 1

Pseudomonas AM 1 is grown in 500 ml E-flasks on a mechanical shaker, at a temperature of 25°C and containing 100 ml substrate of the following composition:

| | |
|---|---|
| $KH_2PO_4$ | 1.4 g/liter |
| $Na_2HPO_4$ | 5.4 g/liter |
| $(NH_4)_2SO_4$ | 0.5 g/liter |
| $MgSO_4 . 7 H_2O$ | 0.2 g/liter |
| $CaCl_2$ | 7.4 mg/liter |
| $FeSO_4 . 7 H_2O$ | 5.0 mg/liter |
| $Na_2MoO_4 . 2H_2O$ | 2.5 mg/liter |
| $MnSO_4 . H_2O$ | 1.8 mg/liter |
| Methanol | 5 g/liter |

After the microorganism has grown out 11.2 mg of indole is added, and after 48 hours of growth 3.3 mg of tryptophan is obtained which corresponds to an exchange of 17 % calculated on added indole.

EXAMPLE 2

The microorganism Pseudomonas AM 1 is grown aerobically in a fermentor on a substrate of the same composition as in example 1. By titration with ammonia, the pH is kept at 6.7. The growing temperature is 28°C. To a substratet quantity of 2 l, 510 mg of indole is added in two positions. After 72 hours of fermentation 490 mg tryptophan is obtained which corresponds to an exchange of 55 % calculated on the added quantity of indole.

EXAMPLE 3

The microorganism methylomonas methanolica is grown on the mechanical shaker (240 rpm) in 500 ml E-flasks with 100 ml substrate volumes in each flask. The composition of the substrate is the same as in example 1. The growing temperature is 25°C. An addition of 15 mg of indole gave 11.3 mg tryptophan after 80 hours of fermentation, which corresponds to an exchange of 43 % calculated on the quantity of added indole.

EXAMPLE 4

The microorganism methylomonas methanolica is grown aerobically in a fermentor on a substrate of the same composition as in example 1. By titration with ammonia the pH is kept at 6.8. The growing temperature is 30°C. To a substrate volume of 2 l, 48 mg indole was added in two portions. After 60 hours fermentation 50 mg tryptophan was obtained, which corresponds to an exchange of 65 % calculated on the quantity of added indole.

EXAMPLE 5

The microorganism Pseudomonas AM 1 is grown in flasks on the shaker. The substrate has the same composition as in Example 1. Different derivatives of indole are added to an initial concentration of 100 mg/l.

After 24, 48 and 72 hours of fermentation, the medium was analyzed and found to contain 5-Hydroxytryptophan, 5-methoxytryptophan, 5-methyltryptophan and 7-methyltryptophan, which were built out of the corresponding indole derivative.

EXAMPLE 6

The same process for the growing of the microorganisms was carried out as in Example 5 but with the difference that the microorganism methylomonas methanolica was used instead.

In the same way as in example 5 it can be stated that the different indole derivatives changed to the corresponding tryptophan derivatives.

EXAMPLE 7

A methanol utilizing candida species which was isolated at the Institute for Biochemistry and Biotechnical Tecnology at the Tekniska Hogskolan, Stockholm, was examined by isotope-technique and was shown that it incorporated methanol in sugar phosphates faster than in amino acids. By the growing of this microorganism in a medium containing inorganic salts, methanol, Thiamine, Biotine, yeast extract and malt extract, the building up of tryptophan could not be demonstrated after incubation with indole (50 and 100 mg/l) within 72 hours after the addition of indole.

EXAMPLE 8

The microorganism pseudomonas AM 1 is grown in 500 ml E-flasks on a shaker containing 100 ml of substrate in each flask with a substrate composition the same as in Example 1, but furthermore an addition of glycine to a concentration equivalent 0,5 g/l. With an addition of 15 mg indole and after 48 hours fermentation, 13.3 mg of tryptophan was obtained, which corresponds to an exchange of 51 % calculated on the quantity of added indole.

We claim:

1. Method for fermentative preparation of 1-Tryptophan and derivative of the general formula

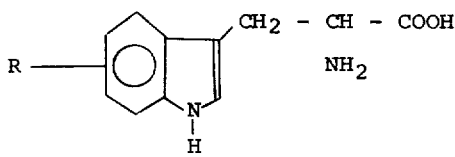

where R is hydrogen, hydroxyl, alkyl or alkoxy groups from indole or indole derivative of the general formula

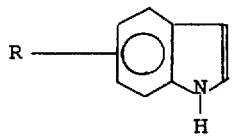

where R has the same meaning as above, characterized in that the fermentation is carried out in a substrate consisting essentially of methanol as the main source for carbon and is carried out using methanol using bacteria of a type that assimilates methanol in such a way that the methanol after oxidation reacts with intracellular glycine, whereby serine is formed.

2. The method of claim 1 wherein the only carbon source for the bacteria consists of methanol.

3. The method of claim 2 wherein said bacteria belongs to the families Pseudomonas and Methylomonas.

4. The method of claim 2 wherein said bacteria is Pseudomonas AM 1.

5. The method of claim 2 wherein said bacteria is Methylmonas Methanolica.

6. The method of claim 1 wherein glycine is added.

7. The method of claim 1 wherein said bacteria belongs to the families Pseudomonas and Methylomonas.

8. The method of claim 1 wherein said bacteria is Pseudomonas AM 1.

9. The method of claim 1 wherein said bacteria is Methylomonas Methanolica.

10. The method of claim 1 wherein said fermentation is carried out under aerobic conditions.

11. The method of claim 1 wherein said fermentation is carried out at a temperature between 18°–45° C.

12. The method of claim 1 wherein said fermentation is carried out at a pH of 5.5 – 8.5.

13. The method of claim 1 wherein said fermentation is carried out at a temperature of 25°– 30° C.

14. The method of claim 1 wherein said fermentation is carried out at a pH of 6.5 – 7.5.

15. The method of claim 1 wherein the fermentation is carried out with 0.1 – 1.0% by volume of methanol.

16. The method of claim 1 wherein the fermentation is carried out with about 0.5% by volume of methanol.

17. The method of claim 1 wherein said fermentation is a continuous process.

18. The method of claim 1 wherein the concentration of free indole in the culture medium is below 500 mg/l.

19. The method of claim 1 wherein the fermentation is a batch process carried out for 30 – 90 hours.

20. The method of claim 1 wherein 1-Tryptophan is prepared.

21. The method of claim 1 wherein said derivative of 1-Tryptophan is selected from the group consisting of 5-hydroxy-tryptophan, 5-methoxy tryptophan, 5-methyl tryptophan, and 7-methyl tryptophan.

* * * * *

UNITED STATES PATENT AND TRADEMARK OFFICE
CERTIFICATE OF CORRECTION

PATENT NO. : 3,963,572
DATED : June 15, 1976
INVENTOR(S) : Gatenbeck et al

It is certified that error appears in the above-identified patent and that said Letters Patent are hereby corrected as shown below:

In column 1, after line 37, insert the following:

--$CH_3OH \longrightarrow CH_2O$
    methanol formadehyde
$CH_2O + THF \longrightarrow$ formyl - THF tetrahydrofolicacid: $CHO$ + glycine $\longrightarrow$ Serine + tetrahydrofolicacid --

Delete lines 38 and 39.

On line 41, change "methanol" to --serine--.

Delete lines 44-47 and insert therefor:

$$HOCH_2\underset{\underset{serine}{NH_2}}{CH} \cdot COOH \longrightarrow \underset{\underset{acid}{pyruvic}}{CH_3 \cdot COCOOH}$$

$$CH_3 \cdot COCOOH + CO_2 \xrightarrow{red} HOOC \cdot \underset{\underset{malic\ acid}{OH}}{CH_2CH} \cdot COOH$$

UNITED STATES PATENT AND TRADEMARK OFFICE
CERTIFICATE OF CORRECTION

PATENT NO. : 3,963,572
DATED : June 15, 1976
INVENTOR(S) : Gatenbeck et al

It is certified that error appears in the above-identified patent and that said Letters Patent are hereby corrected as shown below:

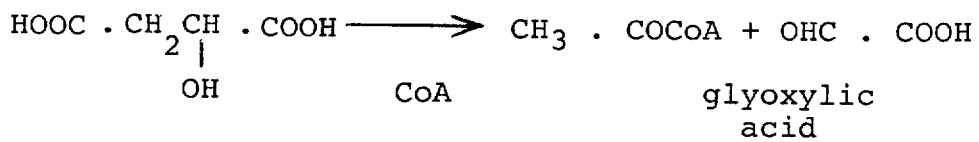

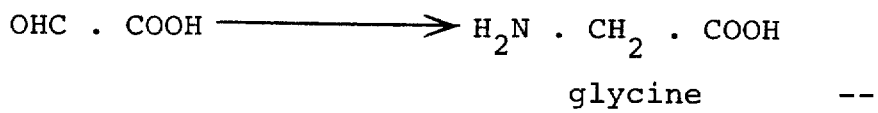

Delete lines 48, 49 and 50 up to and including ".".

In column 2, line 2, insert after "L-serine.", --The building up of serine is an absolute prerequisite in order for the microorganism to be able to utilize methanol as the sole carbon source.-- in column 2, delete lines 14,(from "Ribose-5-phosphate") 15 and 16, inclusive.

insert after the formula of line 22 --Ribose-5-phosphate is built up again through the oxidative decomposition of glucose and according to the pentose cycle.--

In column 3, line 41, delete "much cheaper" and insert therefor --cheap-- in line 42, delete "partly steers the" ; delete "metabolism towards an" and insert therefor --with--.

UNITED STATES PATENT AND TRADEMARK OFFICE
CERTIFICATE OF CORRECTION

PATENT NO. : 3,963,572
DATED : June 15, 1976
INVENTOR(S) : Gatenbeck et al

It is certified that error appears in the above-identified patent and that said Letters Patent are hereby corrected as shown below:

In column 3, line 45, change "derivative" to --derivatives--.

The above amendments are merely to overcome some inadvertent typographical errors and to present the patent in more proper idiomatic English. The amendment concerning synthesis of glycine from serine instead of methanol, see column 1, line 41, is to render the patent more accurate. The synthesis of glycine from serine such as using the enzyme hydroxymethyltransferase is well known as exemplified by Archives of Biochem. Biophys. 146, 461-466 (1971); J. Biol. Chem., Vol. 247, No. 2, pp. 348-52 (1972) and Principles of Biochemistry, page. 502.

Signed and Sealed this

Tenth Day of October 1978

[SEAL]

Attest:

RUTH C. MASON
Attesting Officer

DONALD W. BANNER
Commissioner of Patents and Trademarks